United States Patent [19]

Joo

[11] Patent Number: 4,757,002
[45] Date of Patent: * Jul. 12, 1988

[54] METHOD AND KIT FOR THE ESTIMATION OF SERUM IMMUNOGLOBULIN

[75] Inventor: Han Joo, St. Paul, Minn.

[73] Assignee: Regents of the University of Minnesota, Minneapolis, Minn.

[*] Notice: The portion of the term of this patent subsequent to Dec. 31, 2002 has been disclaimed.

[21] Appl. No.: 814,558

[22] Filed: Dec. 30, 1985

Related U.S. Application Data

[63] Continuation-in-part of Ser. No. 503,824, Jun. 13, 1983, Pat. No. 4,562,147.

[51] Int. Cl.⁴ ............... G01N 33/53; G01N 33/558; C12R 1/445
[52] U.S. Cl. .................. 435/7; 435/810; 435/883; 436/514; 436/515; 436/807; 436/808; 436/809; 436/828
[58] Field of Search ............ 435/7, 810, 30, 36, 435/883; 436/514, 515, 807, 808, 809, 828

[56] References Cited

U.S. PATENT DOCUMENTS

| | | | |
|---|---|---|---|
| 3,947,250 | 3/1976 | Pollack | 436/515 |
| 3,966,897 | 6/1976 | Renn et al. | 424/1.5 |
| 3,995,018 | 11/1976 | Sjöquist | 436/512 |
| 4,617,262 | 10/1986 | Maxim et al. | 435/7 |

OTHER PUBLICATIONS

Chemical Abstracts, vol. 83, 1975, Abstract No. 76830e, Bokhout.
Chemical Abstracts, vol. 73, 1970, Abstract No. 53957f, Heiner et al.
Chemical Abstracts, vol. 97, 1982, Abstract No. 125430z, Kajita et al.
Biological Abstracts, vol. 82, 1986, Abstract No. 23851, Schwan et al.
Am J. Vet. Res. vol. 45, No. 10 (Oct. 1984) Joo et al.

*Primary Examiner*—Robert J. Warden
*Assistant Examiner*—Florina B. Hoffer
*Attorney, Agent, or Firm*—Burd, Bartz & Gutenkauf

[57] ABSTRACT

A radial immunodiffusion enzyme assay method for the simple estimation of immunoglobulins in humans and other animals, Agar test plates are provided including an underlying adherent coating of Staphylococcal Protein A antigen. Blood or blood serum samples from animals to be tested are placed in wells punched in the agar layer and allowed to incubate overnight. The agar gel is then removed. The resulting Protein A antigen layer with bound immunoglobulins from the samples is reacted with enzyme conjugated anti-immunoglobulin or enzyme conjugated Protein A. The reaction is visualized by overlaying the bound conjugate layer with agar containing a color producing enzyme substrate. The diameters of resulting colored zones permit estimation of total immunoglobulins. Methods of preparing Protein A antigen coated test plates are disclosed along with testing kits for carrying out the test procedure in the field.

16 Claims, 2 Drawing Sheets

METHOD AND KIT FOR THE ESTIMATION OF SERUM IMMUNOGLOBULIN

This application is a continuation-in-part of my copending application Ser. No. 503,824, filed June 13, 1983, now U.S. Pat. No. 4,562,147, issued Dec. 31, 1985.

BACKGROUND OF THE INVENTION

1. Field of the Invention

This invention is directed to a method and kit for the estimation of serum immunoglobulin in living beings.

In human and veterinary medicine, it is sometimes desirable to quantify the amount of serum immunoglobulins (Ig, or antibodies). Newborn animals of many mammalian species have very low levels of Ig, which normally rise during feeding of Ig-rich colostrum. Continued low levels may be diagnostic of insufficient antibody levels in the colostrum or inhibition of passive transfer of the antibodies, and are prognostic of morbidity and mortality during the post natal period. The absence or low level of Ig indicates various types of immunodeficiency, usually but not necessarily associated with dysfunction of antibody-producing cells. Conversely, a normal Ig level is indicative of general good health.

Very high levels of Ig are, for instance, present in cattle naturally infected with foot-and-mouth disease virus, in cats with feline infectious peritonitis, in mink with Aleutian disease and in many other infections. Extremely high levels of Ig can be found in cases of certain tumors of lymphoid cells, such as multiple myeloma. All of the above mentioned diseases have guarded or poor prognosis and the levels of Ig are a useful monitor of the disease or therapy therefor.

Most infectious diseases, chronic diseases in particular, will lead to hyperimmunoglobulinemia. This condition is an important defense against infection and will disappear during recuperation. Thus, it is a favorable feature.

THE PRIOR ART

Several techniques are available to quantify serum Ig. For example, electrophoresis requires only microliters of serum sample and gives a relatively accurate percentage estimate of all serum protein fractions. However, the proportion of the Ig must be accompanied by a total serum protein assay, so that the absolute amount of Ig can be known. Also, electrophoresis tends to underestimate extremely high concentrations because of "overflow" from one protein fraction into the region of another. This method requires the use of sophisticated equipment and, therefore, must be performed in a laboratory.

A single radial immunodiffusion is a diffusion procedure in which the serum sample being tested for presence of an Ig diffuses through an agarose gel containing species-specific antiserum against the given Ig. Each test plate for detecting the Ig concentration is supplied with standard of known Ig concentration. Ig from the sample diffuses into the gel until the critical ratio of Ig and anti-Ig is reached, whereupon a precipitate develops. The precipitation ring radius developed by a given serum sample in a given time is compared. High specificity antisera must be used for reproducible results. Such antisera and the necessary standardizations are expensive. Since the antisera are species specific, a different test plate must be used for each species. (A description of these techniques can be found in Barta, Laboratory Techniques of Veterinary Clinical Immunology: A Review, Comp. Immun. Microbiol. Infect. Dis., Vol. 4, No. 2, pp. 131–160, 1981).

In recent years, it has been discovered that a cellwall constituent of Staphylococcus aureus, termed Protein A (as described by Lindmark et al, J. Immun. Meth., Binding of Immunoglobulins to Protein A and Immunoglobulin Levels in Mammalian Sera, Vol. 62, pp. 1–13, 1983) can react with IgG from all mammalian species. The N-terminal region of Protein A consists of 4 globins, highly homologous units which bind to the Fc part of the IgG molecule. Among the 65 different mammalian species so far tested in detail are: human, monkey, rabbit, pig, dog, cat, bovine, mouse, horse, sheep, goat and rat. The degree of reactivity with the predominant class, IgG, when compared to the reactivity with specific antigen, varies from 100% in the human to less than 50% in the sheep. Because of this variation in reactivity, Protein A cannot be used to replace the species specific antibodies in the Agarose gel of the immunodiffusion method.

Applicant's copending application Ser. No. 503,824 discloses a radial immunodiffusion enzyme assay (RIDEA) technique for the diagnosis of pseudorabies in swine by the detection of antibodies to pseudorabies virus. The technique is simple and inexpensive to perform and gives the results overnight. Because of its simplicity, the test can be carried out on the farm by persons with little laboratory experience.

SUMMARY OF THE INVENTION

It has been discovered by applicant that Staphylococcal Protein A can be used as the antigen in his RIDEA assay in order to quantify total serum Ig. According to the invention, Protein A antigen is obtained by preparation or purchase. The Protein A antigen is diluted in a carbonate coating buffer and is allowed to adsorb onto the supporting surface of a test plate (e.g., petri dish). An agar layer is applied and permitted to solidify. A plurality of test sample receiving wells are formed by removing a plug of the agar layer.

Test samples of whole blood or blood serum drawn from the living subjects to be tested and standard control samples are placed in the wells of the test plate, and incubated. The immunoglobulins in the test and control samples diffuse out into the agar at a rate proportional to their concentration in the sample and become bound to the Protein A antigen layer during the incubation period. The agar gel layer then is removed. The remaining Protein A outside the diffusion ring is blocked by application of a blocking serum. A conjugate in the form of an enzyme linked anti-immunoglobulin specific to the species being tested is applied to the Protein A antigen-immunoglobulin layer, and incubated. A further agar layer mixed with an enzyme substrate is applied over the Protein A antigen-immunoglobulin-conjugate layer.

A reaction occurs between the substrate in the agar layer and conjugate producing a colored ring within a few minutes. The diameter of the ring, which is proportional to the concentration of immunoglobulin, is measured and the immunoglobulin quantity is interpreted by plotting the diameters of control and test samples.

The immunoglobulin assay of this invention shares the advantages of the pseudorabies test in that it is simple, inexpensive and easy to perform. Since the parameter to be measured, distance of diffusion, depends only on the concentration of Ig, lessened reactivity with Protein A results in a less intensively colored ring, which does not affect the accuracy of the test, such as the 50% reactivity observed with sheep Ig. It has the additional advantages over the prior art in that one single test plate can be used for any species, thereby decreasing cost, effort and inventory space. A further advantage of the method is that the test sample can be whole blood, thereby eliminating the serum separation step.

The components used in carrying out the test procedure are preferably prepared and packaged as a kit. These include pre-prepared Protein A antigen coated-agar test plates, concentrated washing solution, conjugated immunoglobulin, agar, enzyme substrate and positive and negative control sera.

BRIEF DESCRIPTION OF THE DRAWINGS

The invention is illustrated schematically in the accompanying drawings in which the same numerals refer to corresponding parts and in which.

DETAILED DESCRIPTION OF THE PREFERRED EMBODIMENT

Figure 1:
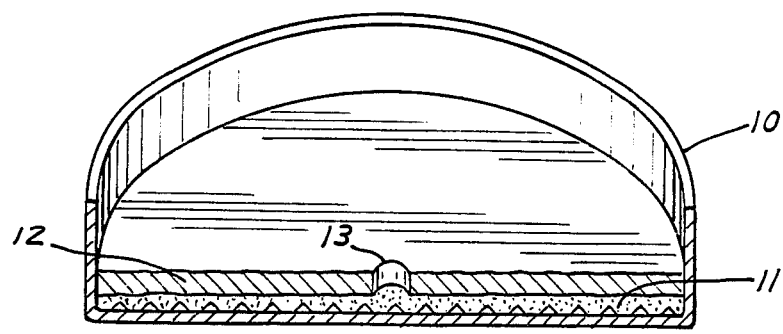
FIG. 1 is a perspective view, partly in vertical section, of a petri dish test plate.

Preparation of Test Plates. Staphylococcal Protein A antigen for use in production of test plates for determination of immunoglobulins may be prepared by purification from *Staphylococcus aureus,* preferably Cowan Strain 1. More conveniently, it can be bought (e.g. from Sigma Biochemicals, St. Louis, Mo., Soluble Protein A, Catalog numbers P6650, P9267 or P8143). The antigen is dissolved in carbonate coating buffer at a concentration of about 5 to 10 $\mu$g/ml and applied as a layer to a suitable supporting surface. Preferably polystyrene or glass petri dishes 10 (FIG. 1) or similar flat receptacles are used for this purpose. The supporting surface is preferably washed with ethanol. After drying, a solution of Protein A antigen is applied to the clean surface and allowed to adsorb onto the test plate for three to seven days.

The Protein A antigen is diluted to an optimum concentration between about 0.01 to 0.001%, preferably in a sodium bicarbonate-sodium carbonate coating buffer to promote adherence of the antigen coating 11 to the supporting surface. The coating buffer should preferably be between about 0.01M to 0.1M (pH 9 to 10) containing from about 0.84 to 8.4 grams per liter of $NaHCO_3$ and 0.11 to 10.6 grams per liter of $Na_2CO_3$. After formation of the adsorbed antigen layer 11, the excess solution is poured off. The antigen coating 11 may be washed with distilled water.

A melted agar layer 12 is applied and permitted to solidify. The depth of the agar layer is not critical. It should be at least about 1.5 mm and preferably about 2 mm up to about 10 mm. The agar layer is applied from solution between about 0.75 to 1.5% and preferably about 1%. A plurality of small diameter holes 13, are punched out of the solid agar to function as test sample wells. The wells may be about 1 to 4 mm in diameter, for example, and penetrate through the agar coating. Preferably the wells are about 3 mm. The prepared test plates are maintained clean and moist by being kept covered until ready for use. They may be sealed, for example, in a non-pervious foil or plastic pouch.

Testing Procedure: A measured amount of whole blood or blood serum from an animal to be tested, including humans, is placed in a well of a test plate. Preferably a sample of 15 $\mu$is used when the well diameter is 2 mm. Three positive control serum samples from the same species as the test sample should be run on each test plate. Known Ig standards from various species are commercially available. The same amount of control serum is placed in other wells on the test plate. The test sample is allowed to diffuse and react overnight at room temperature. The plates may be incubated for between about 6 and 24 hours. During incubation the test serum or blood added to the wells radially diffuses through the agar proportionately to the concentration of immunoglobulins in the test samples and in the animals from which the samples are taken and the immunoglobulins bind to the Protein A antigen.

Figure 2:
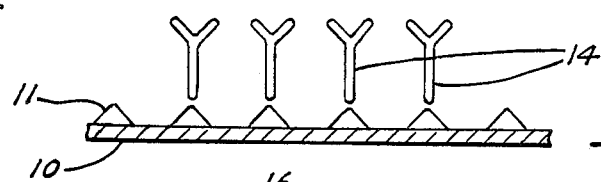
FIG. 2 shows schematically, on a greatly enlarged scale, the binding of test sample immunoglobulin to Protein A antigen.

After incubation of the plates, the agar gel layer is peeled off and it is necessary to block remaining Protein A (outside the diffusion ring) with blocking serum, which is phosphate buffered saline with 10% serum from an animal other than the one tested. Rabbit serum is usually used. The blocking serum is allowed to adsorb for $\frac{1}{2}$ hour at room temperature. As seen schematically in FIG. 2, the immunoglobulins 14 that have reached the antigen layer 11 are bound to it. Antigen layer 11 in turn adheres to the supporting surface 10.

Figure 3:
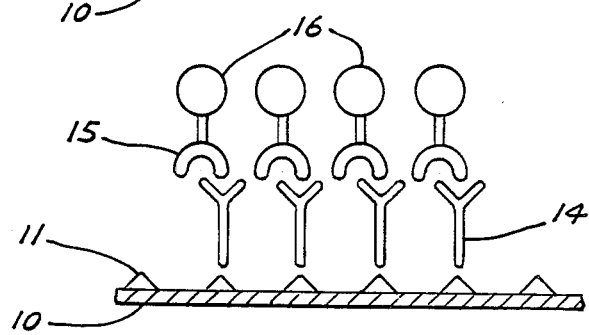
FIG. 3 similarly shows schematically the binding of an enzyme linked anti-immunoglobulin conjugate to the test sample.

A conjugate in the form of a species specific enzyme linked anti-immunoglobulin is applied to the test plate. The conjugate is an anti-immunoglobulin specific to the species being tested having an enzyme chemically bound (conjugated) to it. As seen schematically in FIG. 3, the anti-immunoglobulin 15 with bound enzyme 16 binds to the antibodies 14 adhering to the antigen layer. The conjugate is diluted. Although a special diluent is not needed, the conjugate is diluted preferably with a buffer such as Tween 20 in phosphate buffered saline. Alternatively, phosphate buffered saline with bovine serum albumin, or even water, may be used. Where it is desired for convenience to test several different animal species at the same time, an enzyme conjugated to Protein A is used. This non-specific conjugate produces results comparable to those obtained using the specific antispecies immunoglobulin.

The enzyme can be any one of a number which react with a substrate to produce a colored compound. For example, peroxidase, such as that obtained from horseradish, produces a purple color when reacted with aminosalicylic acid and hydrogen peroxide, or p-phenylene diamine and hydrogen peroxide. Alkaline phosphatase produces a yellow color when reacted with dinitrophenylphosphate. Beta-galactosidase reacts with o-nitrophenyl-$\beta$-D-galactopyranoside to give a purple color.

Conjugates are commercially available. Most are made in the goat or rabbit.

The conjugate applied to the anti-immunoglobulins is maintained for about 30 minutes to 2 hours at room temperature. The plates are then washed, preferably with buffered washing solution to remove any unbound conjugate. Preferably the washing liquid is added slowly from the edge of the test plate with a syringe or pipette and poured off. This should desirably be repeated three times.

While the conjugate is incubating, a second agar coating is prepared. A 1% solution of agar, preferably in phosphate buffered saline, is melted and a substrate for the enzyme of the conjugate is incorporated. A catalyst is incorporated as needed. For example, when the enzyme is a peroxidase, the 1% agar solution may contain between about 0.05 to 0.10% of 5-aminosalicylic acid as the substrate and between about 0.002 and 0.01% hydrogen peroxide as catalyst, and preferably about 0.08% substrate and 0.005% catalyst.

Figure 4:
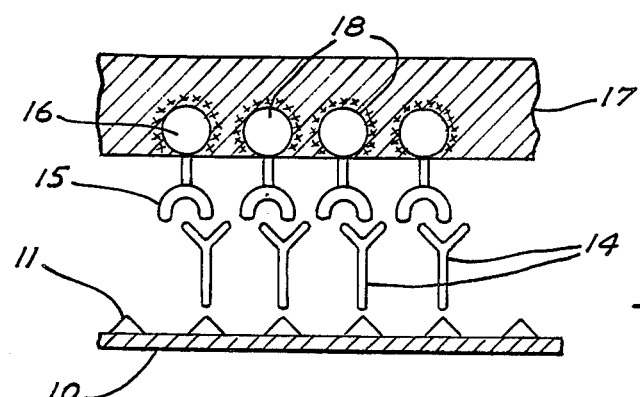
FIG. 4 similarly shows schematically an applied enzyme substrate-containing agar layer and development of a colored reaction product therein.
Figure 5:
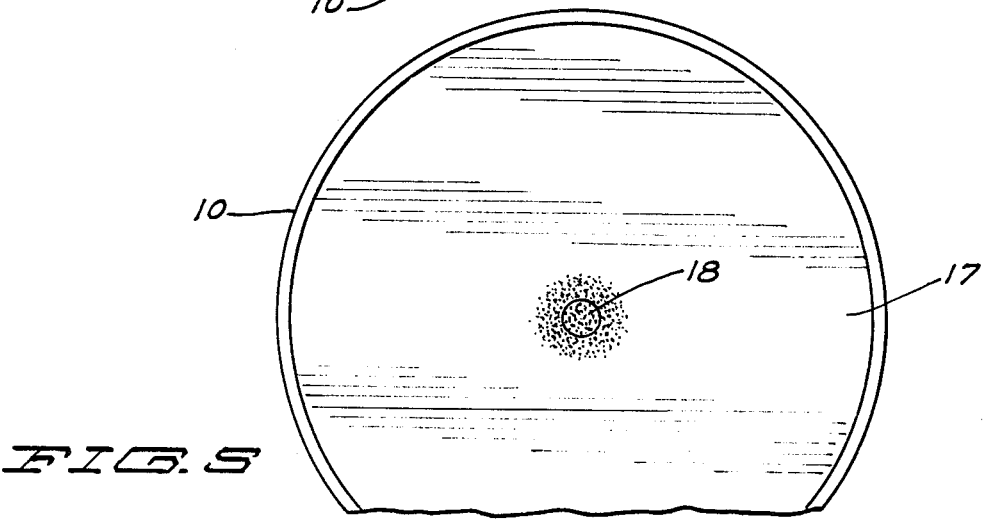
FIG. 5 is a plan view of a petri dish test plate showing schematically the formation of a colored ring for assay evaluation.
Figure 6:
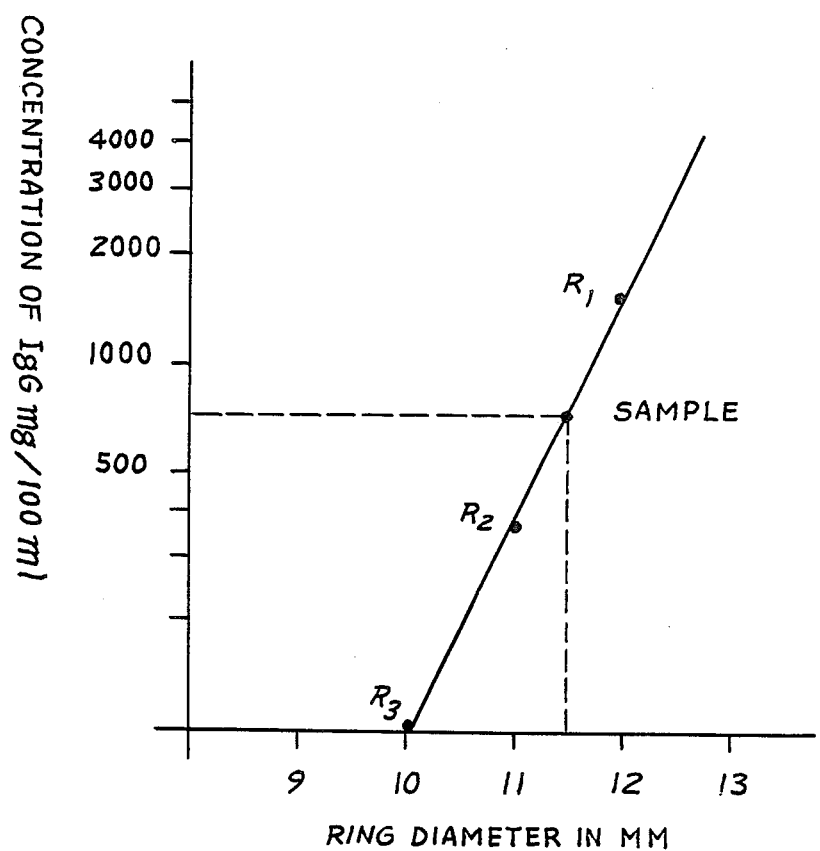
FIG. 6 is an exemplary graph plotted on semilogarithmic paper showing the determination of immunoglobulin concentration.

The agar is poured over the washed conjugate and allowed to solidify. As shown schematically in FIG. 4, a color reaction between the enzyme 16 of the conjugate occurs within the agar support layer 17, as shown at 18. As shown in FIG. 5, the color develops in the form of a circular zone or ring. The rings are dark enough to measure within about 10 to 20 minutes of the substrate reaction. Upon standing, the ring will become darker but will not become larger. The diameter of the ring produced is related to the amount of immunoglobulin present in the blood. The diameters of the dark colored circular zones of the 3 control sera are measured and plotted with the Ig quantities of those samples and make a standard line on a semi-logarithmic paper. The diameters of the test sera are plotted on the standard line and the Ig quantity of the test samples is read. This is illustrated in FIG. 6 wherein $R_1$, $R_2$ and $R_3$ represent diameters of color zones produced by standard control sera of known Ig concentration.

For ease of administration of the diagnostic test in the field, the materials are preferably assembled in a kit. Such a kit includes previously prepared test plates, solid agar, concentrated washing solution, conjugate, substrate, catalyst, positive control serums, blocking serum and instructions for use including semi-logarithmic paper for plotting data and for interpretation of the results. The size and quantity of the components depends upon the size of the group to be tested.

The invention is further illustrated by the following examples:

EXAMPLE 1

The preparation of the test plates is illustrated by the following: A stock solution of Protein A (10 mg. Soluble Protein A, Catalog No. P6650, Sigma Biochemicals, St. Louis, Mo., dissolved in 1 ml distilled water) is diluted 1:1000 in Coating Buffer (0.1M $NaHCO_3$+0.05M $Na_2CO_3$, pH 9.6). 60 mm polystyrene test dishes are prewashed with 95% ethanol for ten minutes and placed on a level surface. After drying, 3 ml of the antigen preparation is pipetted into each dish and allowed to adsorb at 4° C. for 3 to 7 days. The excess is poured off. 10 ml of distilled water is added gently, one edge with a pipette, swirled gently over the surface, and carefully poured off. A 1% agar (Difco purified in PBS, phosphate buffered saline, 0.05M, pH 7.4) is heated until melted, and 6 ml added to each dish. After the agar solidifies, 3 mm diameter holes are punched out of the solid agar. The dishes are covered until used and stored at 4° C.

EXAMPLE 2

The procedure for testing is illustrated by the following: Porcine blood is drawn into a test tube and allowed to clot. 15 μl of the test serum is added to one well of the dish. The same size sample of porcine reference standard sera (Cappel-Worthington Biomedicals, Malvern, Pa.) containing less than 100 (R3), 375 (R2) or 1500 (R1) mgIgG/100 ml of serum are added to other wells on the same test dish. After addition of the samples, the dishes are covered with lids and kept at room temperature for 18 hours. The timing of this step is not critical and can be from 6 to 24 hours, since the reference sera was run on each dish.

The agar is stripped from the dish by lifting one edge and then peeling the agar off. The unreacted Protein A is blocked by adding PBS containing 10% rabbit serum. The blocking serum is allowed to adsorb to the excess Protein A for 30 minutes at room temperature. The dish is then washed three times by carefully adding 5 ml of Washing Buffer [PBS+0.5% Tween-20 (Sigma)] to the edge of the dish, swirling it gently over the surface and carefully pouring it off. Conjugate is prepared by mixing one premeasured vial of rabbit anti-swine immunoglobulin conjugated to horse-radish peroxidase (Cappel-Worthington) with 12 ml of Washing Buffer. The amount of conjugate supplied in one vial is empirically determined to be the least amount that, when mixed with 12 ml of diluent and used in the test, will result in rapidly developing rings with sharp edges, against an acceptable contrasting background. 3 ml of this solution is added to each dish and binding allowed to proceed for 45–60 minutes. The timing of this step is not critical, as intensity but not diameter of the resulting rings will be affected. While the dishes are incubating, 25 ml of 1% agar in PBS is melted and cooled until it is just slightly warm to the touch. The conjugate is poured off slowly and the dish washed as above. Substrate (to give a final concentration of 0.08% amino salicylic acid and 0.05% $H_2O_2$) is added to the agar solution and mixed quickly. 5 ml of the solution is added immediately to the dish. The agar is allowed to solidify and the color to develop. The rings are dark enough to measure within ten minutes. Longer time will give darker but not larger rings. The diameters of the rings are measured and the diameters of the reference sera are plotted on the abscissa of semi-log graph paper against the concentration in mg/100 ml on the ordinate and a standard line drawn (FIG. 6). The concentration of the test serum is read off of the standard line. Alternatively, the coefficient of regression of the standard line may be calculated and the concentration of the test serum calculated manually or by electronic means. An example is shown in Table 1.

TABLE 1

Mean diameters of reference porcine IgG in protein A RIDEA by different incubation times

| Porcine IgG (mg/100 ml) | Incubation hours at 25° C. | | | |
|---|---|---|---|---|
| | 6 | 12 | 18 | 24 |
| 500 | 11.0 | 14.6 | 16.7 | 18.3 |
| 50 | 9.0 | 11.7 | 12.6 | 14.0 |
| 25 | 9.0 | 11.2 | 12.8 | 13.8 |
| 5 | 6.8 | 7.8 | 8.8 | 8.8 |
| 2.5 | 6.3 | 7.5 | 8.2 | 8.3 |

Mean diameters of 3 tests

EXAMPLE 3

The testing procedure of Example 2 is repeated using whole blood in place of serum. The animal to be tested is pricked on the ear with a stylet. A drop of blood is drawn into a heparinized capillary tube with a marking of 15 μl. A separate sample is drawn into a hematocrit tube. The sample is tested as in Example 2. The hematocrit tube is centrifuged at 3000 for 10 min. and the proportion of plasma noted. The results as determined by the method of Example 2 are corrected for volume. For example, if the apparent value is 500 mg/100 ml and the hematocrit is 0.35, then the true serum value is 500/0.65 or 769 mg.

EXAMPLE 4

Several different animal species may be tested at the same time for convenience, as seen in Table 2. Test plates are prepared according to the method of Example 1 using peroxidase conjugated to Protein A, in the same manner as in Example 2. Results are comparable to those obtained using the specific antispecies immunoglobulin, as seen in Table 3.

TABLE 2

Comparison of RIDEA diameters using test dishes prepared with different sources of protein A.

| reference | IgG(mg/100 ml) | test dish A(s,p-6650) | lot B(s,p-8143) | C(crude prep.) |
|---|---|---|---|---|
| Bovine | | | | |
| 1 | 1800 | 8.0 | 7.5 | 6.0* |
| 2 | 450 | 7.0 | 7.0 | 5.0* |
| 3 | 113 | 5.5 | 5.0 | 4.0* |
| Swine | | | | |
| 1 | 1500 | 12.0 | 12.0 | 12.0 |
| 2 | 375 | 11.0 | 11.0 | 11.0 |
| 3 | 94 | 10.0 | 10.0 | 10.0 |
| Horse | | | | |
| 1 | 2000 | 9.0 | 9.0 | 8.0 |
| 2 | 500 | 7.5 | 8.0 | 5.5* |
| 3 | 125 | 5.5 | 6.0 | 5.0 |
| Dog | | | | |
| 1 | 2700 | 13.0 | 13.0 | 8.0* |
| 2 | 675 | 12.0 | 12.0 | 5.5* |
| 3 | 169 | 11.0 | 11.0 | 5.0* |
| Cat | | | | |
| 1 | 1400 | 12.0 | 12.0 | 12.0 |
| 2 | 350 | 11.0 | 11.0 | 11.0 |
| 3 | 87 | 10.0 | 10.0 | 10.0 |

*over 1 mm in diameter disagreement between test dishes

TABLE 3

Comparison of protein A RIDEA diameters using different peroxidase conjugates

| Reference IgG | Conjugated peroxidase to Anti-species IgG | protein A |
|---|---|---|
| Bovine | | |
| 1 | 8.3 | 7.8 |
| 2 | 6.3 | 5.3 |
| 3 | 4.3 | 3.5 |
| Swine | | |
| 1 | 15.0 | 14.5 |
| 2 | 13.5 | 13.0 |
| 3 | 12.0 | 11.5 |
| Horse | | |
| 1 | 9.0 | 6.5* |
| 2 | 8.0 | 5.0* |
| 3 | 5.8 | 3.5* |
| Dog | | |
| 1 | 16.0 | 13.0* |
| 2 | 14.0 | 12.0* |
| 3 | 13.0 | 11.0* |
| Cat | | |
| 1 | 16.0 | 15.0 |
| 2 | 14.0 | 12.0* |
| 3 | 12.0 | 11.0 |

*over 1 mm in diameter disagreement

It is apparent that many modifications and variations of this invention as hereinbefore set forth may be made without departing from the spirit and scope thereof. The specific embodiments described are given by way of example only, and the invention is limited only by the terms of the appended claims.

I claim:

1. A method of quantitatively estimating serum immunoglobulins in animals by reacting immunoglobulins with Staphylococcal Protein A, which method comprises:
   (A) placing a sample of blood or blood serum drawn from an animal in a sample well of a test plate comprising:
      (1) a supporting surface,
      (2) a coating adsorbed on said surface of Protein A antigen,
      (3) a layer of agar overlying said Protein A antigen coating, and
      (4) a plurality of sample-receiving wells extending through the agar layer,
   (B) placing a plurality of positive control sera samples of known immunoglobulin quantities from the same animal species in other sample wells of said test plate,
   (C) incubating said samples to bind immunoglobulins from the samples to the Protein A antigen layer,
   (D) removing the agar layer and applying a blocking serum over the Protein A antigen layer with bound immunoglobulins,
   (E) applying a conjugate, an enzyme linked species specific anti-immunoglobulin or enzyme linked Protein A to said bound immunoglobulins and incubating to bind the conjugate to the immunoglobulins,
   (F) applying an agar layer containing a color producing substrate for the conjugate over the bound conjugate,
   (G) measuring the diameters of the resulting colored reaction zones,
   (H) plotting the diameters and known immunoglobulin quantities of the control samples to form a standard line, and
   (I) reading the immunoglubulin quantities of the test samples by plotting the diameters of the test samples on the standard line.

2. A method according to claim 1 wherein incubation is carried out at room temperature.

3. A method according to claim 1 wherein said sample in the sample well is incubated at room temperature for about 6 to 24 hours.

4. A method according to claim 1 wherein said applied conjugate is incubated at room temperature for about 45 minutes to 2 hours.

5. A method according to claim 1 wherein said conjugate is peroxidase conjugated rabbit or goat anti-immunoglobulin or peroxidase conjugated Protein A and said substrate is 5-amino-salicylic acid or p-phenylenediamine with hydrogen peroxide catalyst.

6. A test plate for use in the estimation of immunoglobulins which comprises:
(A) a supporting surface,
(B) a coating adsorbed on said supporting surface of Staphylococcal Protein A antigen,
(C) a layer of agar overlying said Protein A antigen coating,
(D) a plurality of sample-receiving wells extending through the agar layer, and
(E) cover means for keeping the test plate clean and moist until time of use.

7. A test plate according to claim 6 wherein the Protein A antigen coating includes as a coating buffer a small amount of sodium bicarbonate and sodium carbonate to promote adhesion to the supporting surface.

8. A test plate according to claim 7 wherein said Protein A antigen coating includes between about 0.08% and 0.84% sodium bicarbonate and between about 0.11% and 1.06% sodium carbonate.

9. A test plate according to claim 6 wherein said test wells are between about 1 and 4 mm in diameter.

10. A test plate according to claim 6 wherein said supporting surface is a polystyrene petri dish.

11. A test plate according to claim 6 which comprises:
(A) a polystyrene supporting surface,
(B) a coating adsorbed on said polystyrene surface of Protein A antigen including as a coating buffer between about 0.08% and 0.84% sodium bicarbonate and between about 0.11% and 1.06% sodium carbonate,
(C) a layer of agar overlying said antigen coating layer,
(D) a plurality of sample receiving wells between about 1 and 4 mm diameter extending through the agar layer, and (E) cover means for keeping the test plate clean and moist until time of use.

12. A test kit for estimating immunoglobulins in animals by reacting immunoglobulins with Staphylococcal Protein A, which kit comprises:
(A) at least one test plate comprising:
  (1) a supporting surface,
  (2) a coating adsorbed on said surface of Protein A antigen,
  (3) a layer of agar overlying said antigen coating,
  (4) a plurality of sample-receiving wells extending through the agar layer, and
  (5) cover means for maintaining the test plate clean and moist until time of use,
(B) a container of a conjugate, an enzyme conjugated anti-immunoglobulin or enzyme conjugated Protein A,
(C) a container of agar,
(D) a container of a color producing substrate for the enzyme of said conjugate for incorporation in said agar, and
(E) instructions for use of the kit including semilogarithmic paper for plotting test data for interpretation of test results.

13. A test kit according to claim 12 wherein the kit includes containers of positive control serums.

14. A method according to claim 1 wherein said blocking serum comprises a phosphate buffered saline solution containing about 10% serum from an animal species other than that being tested.

15. A test kit according to claim 12 wherein the kit includes a container of blocking serum in aqueous solution.

16. A test kit according to claim 12 wherein the kit includes a container of a blocking serum comprising a phosphate buffered saline solution containing about 10% serum from an animal species other than that for which the test kit is designed.

* * * * *

UNITED STATES PATENT AND TRADEMARK OFFICE
CERTIFICATE OF CORRECTION

PATENT NO. : 4,757.002
DATED : July 12, 1988
INVENTOR(S) : Han Soo Joo

It is certified that error appears in the above-identified patent and that said Letters Patent is hereby corrected as shown below:

In the heading, after "Inventor", "Han Joo" should be
-- Han S. Joo --.

Signed and Sealed this

Twenty-fourth Day of January, 1989

Attest:

DONALD J. QUIGG

Attesting Officer      Commissioner of Patents and Trademarks